United States Patent [19]

Wilson

[11] 4,192,312
[45] Mar. 11, 1980

[54] SURGICAL INCISION GUIDE MEANS

[76] Inventor: Donald L. Wilson, 5 Bon Air Rd., Sohner Plz. #127, Larkspur, Calif. 94939

[21] Appl. No.: 938,804

[22] Filed: Sep. 1, 1978

[51] Int. Cl.² ............................................. A61B 19/00
[52] U.S. Cl. .......................... 128/303 R; 128/132 D; 128/305
[58] Field of Search ..................... 128/305, 305.5, 751, 128/630, 303 R, 316, 132 D, 334 R, 335, 335.5

[56] References Cited

U.S. PATENT DOCUMENTS

| 2,556,036 | 6/1951 | Jensen .................................. 128/305 |
| 2,932,296 | 4/1960 | Sanders ................................ 128/305 |
| 3,060,932 | 10/1962 | Pereny et al. ..................... 128/132 D |
| 3,397,692 | 8/1968 | Creager, Jr. et al. ............ 128/132 D |
| 3,502,070 | 3/1970 | Bliss .................................. 128/303 R |
| 3,956,048 | 5/1976 | Nordgren ..................... 128/132 D X |
| 4,114,624 | 9/1978 | Haverstock .......................... 128/335 |

FOREIGN PATENT DOCUMENTS

997975 10/1976 Canada ................................. 128/132 D

*Primary Examiner*—Kyle L. Howell
*Attorney, Agent, or Firm*—John R. Walker, III

[57] ABSTRACT

A patch-like web of material adapted to be placed over skin tumors for aiding a physician in making an optimum size and shape incision when surgically removing the tumor. The web of material is provided with an opening having a predetermined size which correlates with the size of the tumor. Also included are delineation provisions for providing a pattern which prescribes the optimum size and shape for the particular incision.

12 Claims, 8 Drawing Figures

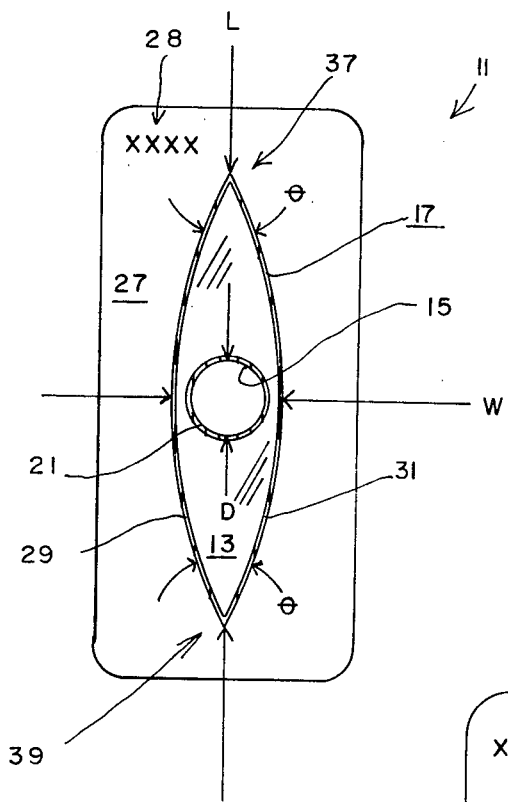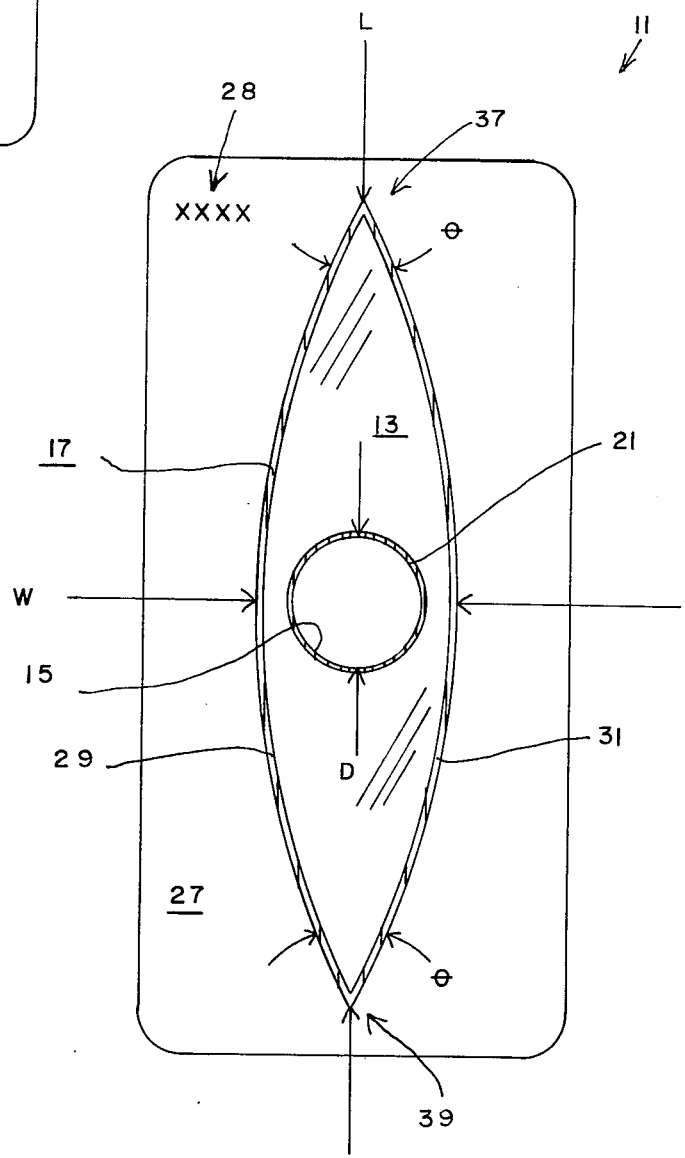

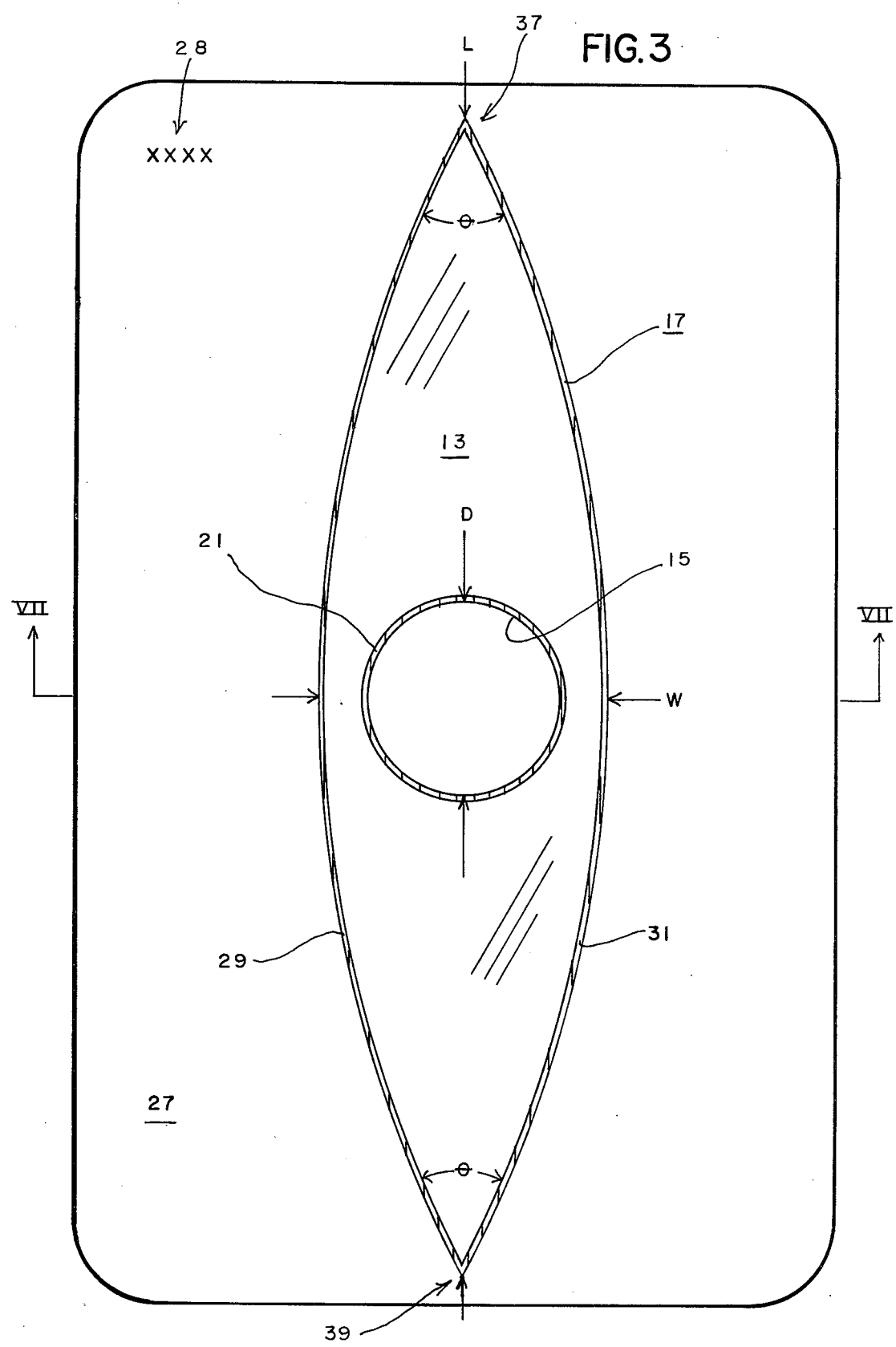

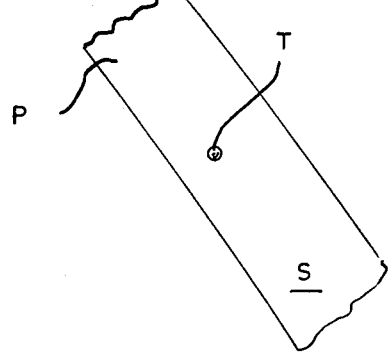
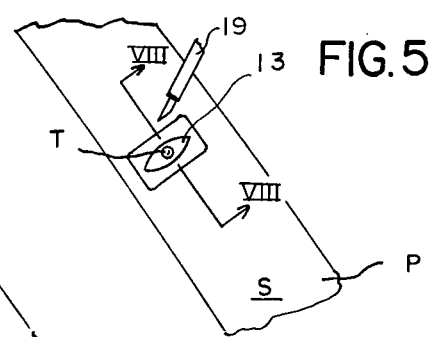
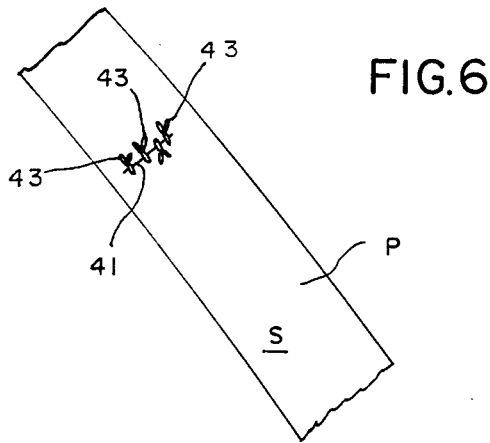
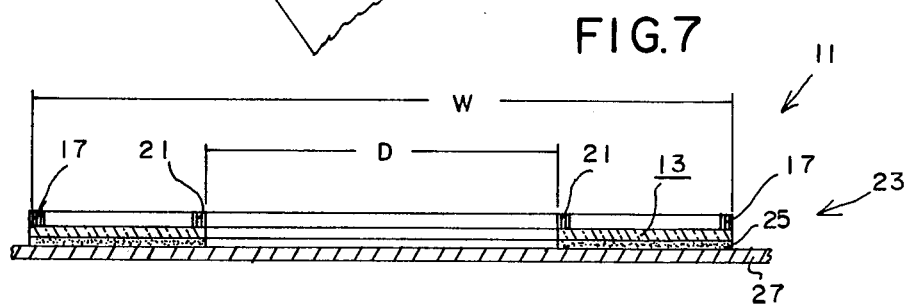
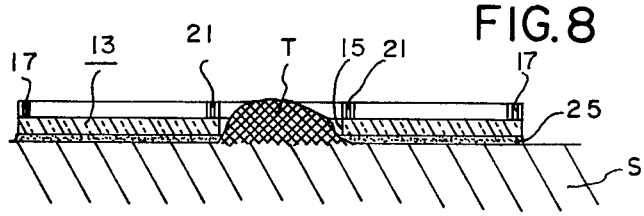

SURGICAL INCISION GUIDE MEANS

BACKGROUND OF THE INVENTION

1. Field of the Invention

This invention relates to the field of incision guide apparatuses.

2. Description of the Prior Art

A skin tumor which requires excision and primary closure usually requires an elliptical excision for effecting a closure that is free of irregularities and so-called "dog ears." The shapes of such ellipses, when made free hand, are often difficult to estimate and perform, especially for larger tumors, e.g., for those over a few millimeters in diameter. Additionally, the dimensions of both the length and width of the elliptical shaped excision, while not critical, are, nonetheless, most significant if a proper closure is to be effected.

More specifically, when a tumor has to be excised from the skin, an ellipse is made around the skin tumor so that the remaining skin defect may be closed in a straight line. If either a circular incision or an incision having one side longer than the other is made around the tumor then upon suturing the skin margins together, a bunching of the ends of the incision takes place. These bunchings are often called "dog ears." In other words, irregular or asymmetrical incisions will surely result in irregular and poor surgical closures of the skin, which, of course, leave unsightly scars.

Most doctors and even experienced surgeons have some difficulty in estimating a perfect elliptical incision, especially for skin tumors larger than 6 millimeters in diameter. If the incisions are not long enough, wide enough, or symmetrical enough, for the size of the tumor being excised, irregular and less cosmetically acceptable closure of the skin results. This problem has previously been recognized in the medical field and attempts have been made, heretofore, to minimize or alleviate the problem. In fact, applicant is aware of the following three U.S. patents which have a bearing on this problem: U.S. Pat. No. 2,932,296 granted to Sanders; U.S. Pat. No. 3,060,932 granted to Pereny et al; and U.S. Pat. No. 3,502,070 granted to Bliss. None of these patents suggest or disclose applicant's device. However, the Bliss patent is more closely associated with the problem at hand.

SUMMARY OF THE INVENTION

The present invention is directed towards overcoming the disadvantages and problems encountered heretofore in skillfully excising a tumor from the skin of a patient. More specifically, the present invention overcomes the problem of trying to estimate a proper size elliptically shaped incision needed to remove most skin tumors which can be excised from the skin and closed primarily. Therefore, the advantages of the device of the present invention are:

(1) It helps prevent the adverse condition previously mentioned and known in the art as "dog ears."

(2) It alleviates the possibility of poor surgical closures for skin tumors up to 18 millimeter diameter (about the size of a dime) that are removed surgically. It will be appreciated by those skilled in the art that since most skin tumors are within this range and are also the tumors which can be removed by primary excision, the device of the present invention will prove to be of great help in making these excisions.

The device of the present invention is preferably made of a transparent film-like substance or clear tape. It is characterized by a conspicuous outer margin, e.g., red in color or such other manner, for indicating the incision area. It preferably also has a conspicuous inner margin, e.g., red in color or the like, surrounding a central opening or cut out area, i.e., which is representative in size of the tumor. The device of the present invention is intended to be provided in a series of approximately 16 different sizes the smallest of which would be a 3 millimeter diameter center opening and progressing at the rate of 1 millimeter each to at least an 18 millimeter diameter center. The devices preferably would be individually packaged with a peel off backing and would be gas sterilized. The diameter of the central opening would preferably be conspicuously affixed to each of the devices so as to readily identify one size from the other, e.g., 15 millimeter, etc.

DESCRIPTION OF THE DRAWINGS

FIGS. 1 through 3, depict in plan view, a series of various different size devices or surgical incision guide means of the present invention, although, FIGS. 2, 3 are enlarged to develop clearly certain details of the device.

FIG. 4 is intended to depict a limb of a patient with a skin tumor shown thereon.

FIG. 5 is intended to depict the limb of the patient with the patch-like means of the present invention being affixed thereto and with a portion of a scapel instrument being shown in proximity therewith.

FIG. 6 depicts the limb of the patient subsequent to the tumor having been surgically removed and the skin margins of the incision being properly sutured.

FIG. 7 is an enlarged sectional view taken as on the line VII—VII of FIG. 3 having the left and right outer portions of the device broken away.

FIG. 8 is an enlarged sectional view taken as on the line VIII—VIII of FIG. 5 which more clearly shows the relationship of the patch-like means with the tumor.

DESCRIPTION OF THE PREFERRED EMBODIMENT

The surgical incision guide means 11 of the present invention is intently directed toward aiding a physician in making an optimum size and shape incision with respect to skin tumors and like ailments. FIGS. 4 through 6 of the drawings respectfully depict portions of patients, as characterized by the letter P, and which might represent limbs of the patient. Additionally, FIGS. 4 and 5 depict what might be regarded as tumors, as characterized by the letter T, while the initial incision, per se, will not be specifically character referenced in the drawings, the shape thereof will readily be apparent as the specification proceeds.

The surgical incision means 11 includes patch-like means 13 for placement upon and contiguously engaging the skin, characterized by the letter S, of the patient P, in a manner clearly shown in FIG. 5.

Particular attention is now directed towards FIGS. 1 through 3 of the drawings wherein it may be seen that, preferably, the patch-like means 13, is elliptically shaped and is provided with an opening, as at 15. The opening 15, being centrally disposed of the elliptically shaped patch-like means 13, aids in placing the patch-like means 13 in an optimum location with respect to the tumor T, as clearly shown in FIG. 8 of the drawings.

The guide means 11 also includes elliptically shaped delineation means, e.g., first indicia means as at 17, for readily providing a pattern which prescribes an optimum size and shape for the particular incision. Accordingly, the shape of the incision is precisely determined by the first indicia means 17.

More specifically, the first indicia means 17 preferably is in the form of a narrow conspicuous continuous band affixed to the patch-like means 13 and which has a prescribed elliptical shape that may readily be traced with a scapel, as at 19 in FIG. 5 of the drawings, and like instruments as the incision is initially being made. In addition, the patch-like means 13 preferably is formed from a flexible material which may readily be applied to various different contoured areas of the body of the patient P, e.g., fingers (not shown) and other like areas.

Moreover, the flexible material, constituting the patch-like means 13, preferably is further characterized by being formed from a transparent film-like substance, e.g., somewhat similar to well known clear tape. Therefore, since the outline of the transparent patch-like means 13 is not inherently readily conspicuous, the first indicia means 17 is an enhancement in that it aids the physician in initially making the optimum size and shape incision. Therefore, the first indicia means 17, being affixed to the patch-like means 13, clearly delineates the outer margin area of the patch-like means 13.

In order to enhance the conspicuousness of the first indicia means 17, it preferably is embodied in any color which stands out, e.g., it might be red in color as graphically indicated in FIGS. 1 through 3. More specifically, the first indicia means 17, being established by the red color, may be applied (or affixed) to the patch-like means 13 in any well known manner and in accordance with the state of the art.

However, it should be understood that it is anticipated that the patch-like means 13 may, in certain other embodiments not shown, have a shape other than elliptical. For example, it might be rectangular or the like. In this event, the first indicia means 17 would, nonetheless, have a size and shape precisely as disclosed in FIGS. 1 through 3. Accordingly, it may be stated that without exception, the first indicia means 17 is elliptically shaped. Accordingly, the first indicia means 17 constitutes the delineation means (alluded to above) for readily providing a pattern which prescribes an optimum size and shape for the particular incision. Of course, in the event the patch-like means 13 has a shape other than elliptical, the film-like structure may readily be severed simultaneously with the skin of the patient when initially making the elliptical shaped incision prescribed therewith.

From FIGS. 1 through 3 of the drawings it should readily be appreciated that the concept of the present invention encompasses a series of guide means 11. In fact, the intent is to provide at least 16 different sizes of patch-like means 13 in which the respective centrally disposed openings 15 thereof have predetermined sizes which correlate with the size of the tumor T and like ailment. More specifically, the size of the opening 15 for the smallest size patch-like means 13, i.e., as suggested in FIG. 2, will be a nominal 3 millimeters in diameter. Further, the sizes progressingly increase in 1 millimeter steps, whereby, the diameter of the opening 15 for the largest size device 11 is a nominal 18 millimeters.

The patch-like means 13 also preferably includes second indicia means, as at 21, which is similar to the first indicia means 17. The second indicia means 21 is in the form of a narrow conspicuous annular band affixed (or applied) to the patch-like means 13 and disposed circumjacent to the central opening 15. More specifically, the second indicia means 21, is also preferably red in color and is applied to the patch-like means 13 in like manner as above described for the first indicia means 17.

Therefore, since the patch-like means 13 is preferably transparent, the second indicia means 21 aids the physician in properly positioning the opening 15 thereof with respect to the tumor T.

From FIGS. 1–3 and 7, 8 of the drawings it may readily be seen that the surgical incision guides means 11 also includes means, e.g., adhesive means as at 23 or like, for enabling the patch-like means 13 to readily be removably attached to the patient's skin S. More specifically, the adhesive means 23 preferably includes a film of pressure sensitive adhesive material, as at 25 in FIGS. 7, 8, which is suitably applied to one side of the patch-like means 13 in a well known manner. Additionally, the adhesive means 23 includes a peel away backing member, as at 27 in FIG. 1–3 and 7 of the drawings. Therefore, the patch-like means 13 is ever ready to be removably attached to the patient's skin S by simply separating the patch-like means 13 from the peel away backing member 27 in a well known manner.

In actual practice, the size of the opening 15 for each patch-like means 13 will preferably be indicated on the backing member 27 associated therewith. In other words, the device 11 preferably includes third indicia means, as at 28 in FIGS. 1–3 of the drawings. The intent of the third indicia means 28 is to facilitate the selection of the optimum size patch-like means 13 with respect to the size of the tumor T. Accordingly, the third indicia means 28 would be in the form of printed characters indicating the particular size opening 15, e.g., 12 millimeters or 13 millimeters, etc.

It will be appreciated by those skilled in the art that the entire surgical incision guide means 11 preferably is sealed in paper or other suitable material, i.e., plastic wrap or the like. Also, it will be properly sterilized in a manner well known in the state of the art so as to remain sterile until opened by the physician.

Particular attention is again directed towards FIGS. 1–3 of the drawings wherein it may be seen that the centrally disposed opening 15 has a diameter D and the delineation means. i.e., the first indicia means 17, is oblong in shape having a major axis L and a minor axis W. Additionally, the magnitude of the minor axis W is a nominal one and one-half times greater than that of the diameter D.

Further, the magnitude of the major axis L is a nominal 6 times greater than that of the diameter D.

Further yet, it may readily be seen that the magnitude of the major axis L is a nominal 4 times greater than that of the minor axis W.

For example, let us consider one such patch-like means having an opening 15 wherein the diameter D thereof equals 12 millimeters. Accordingly, when applying the above criteria, the magnitude of the minor axis W is one and one-half times D (or 1.5×12), thus W equals 18 millimeters. Also, the magnitude of the major axis L is six times D (or 6×12), thus L equals 72 millimeters. Further, the magnitude of the major axis L is four times that of the minor axis W (or 4×18), thus L equals 72 millimeters.

Moreover, it may readily be seen that the oblong shaped delineation means, i.e., the first indicia means 17, terminates abruptly at either end of the major axis L so as to establish a pair of remotely disposed corners, characterized respectively by the numerals 37, 39.

It will be appreciated by those skilled in the art that since the prescribed incision terminates at either end of the major axis L with the corners 37, 39 the closure thereof is greatly simplified, i.e., as opposed to arcuately terminating the major axis L. In other words, the corners 37, 39 contribute significantly to the present invention thus aiding in establishing a closure that is free of irregularities and the sio-called "dog ears." Of course, the other features of the device 11 contribute equally in assuring a closure that is free of irregularities and so-called "dog ears."

OPERATION

The following sequence outlines the steps to be taken in using the surgical incision guide means or device 11 of the present invention:

1. Measure the diameter of the skin tumor T.
2. Prepare the skin S as heretofore required for a skin tumor excision, i.e., in a manner well known to those skilled in the art.
3. Choose the same size ellipse cut out (or opening 15) as the diameter of the tumor T and, after removing the backing member 27, place the elliptically shaped patch-like means 13 over the tumor T with the ends or corners 37, 39 of the patch-like means 13 being placed in alignment with the line of closure, i.e., like that characterized by the numeral 41 in FIG. 6 of the drawings. It will be appreciated by those skilled in the art that the line of closure 41 preferably is selected in such manner that it usually is along the axis of any existing natural wrinkle line. The flexibility of the patch-like means 13 enables it to be molded around irregular areas such as fingers and joints.
4. Make a skin ellipse incision around the skin tumor T by moving the scapel 19 along the delineation means, i,e., the first indicia means 17 which, as previously mentioned, preferably is a red marginal band affixed to the patch-like means 13.
5. Under cut and remove the incised skin which is in the shape of the first indicia means 17 and which has at least that portion of the patch-like means 13 defined by the first indicia means 17 attached thereto.
6. After the surgical removal is complete, the patch-like means 13 may be peeled off the skin specimen, which is then sent to the laboratory for pathological examination.

The following is an exception to step 3: When the skin tumor T is malignant, selection of a surgical incision guide means 11 having a larger diameter opening 15 than that of the tumor T is preferred for added clearance, i.e., this safe guards against leaving any remnants of the tumor T.

7. The skin margin defining the incision are now sutured together by a plurality of stitches (characterized by the numeral 43 in FIG. 6 of the drawings) in any manner well known to those skilled in the art. Thus a bunching of the ends of the incision is precluded, i.e., the skin defect defining the incision may be closed in the straight line 41 (FIG. 6) in such a manner that it is absolutely free of irregularities and so-called "dog ears." Thus, this obviates the problem heretofore encountered when either a circular incision or an incision having one side longer than the other is made around the tumor T which, upon suturing the skin margins together which resulted in a bunching at the ends of the incision, i.e., a well established fact is that irregular or asymmetrically incisions always result in an irregular and poor surgical closure of the skin.

Although the invention has been described and illustrated with respect to a preferred embodiment thereof, it is to be understood that it is not to be so limited since changes and modifications may be made therein which are within the full intended scope of the invention.

I claim:

1. Surgical incision guide means for aiding a physician in making an optimum size and shape incision with respect to skin tumors and like ailments, said guide means comprising patch-like means for placement upon and contiguously engaging the skin of the patient, said patch-like means being provided with an opening centrally disposed thereof for aiding in placing said patch-like means in an optimum location with respect to the tumor, and said guide means including delineation means extending in a substantially elliptical shape for readily providing a substantially elliptical pattern which prescribes an optimum size and shape for the particular incision and for defining the boundary of an area of the patient's skin to be excised.

2. The surgical incision guide means as set forth in claim 1 in which said delineation means includes first indicia means in the form of a narrow conspicuous continuous band affixed to said patch-like means and having a prescribed shape which may readily be traced with a scapel and like instruments as the incision is being made.

3. The surgical incision guide means as set forth in claim 2 in which said centrally disposed opening has a predetermined size which determines the optimum size tumor and like ailment to be excised.

4. The surgical incision guide means as set forth in claim 3 in which is included means for enabling said patch-like means to readily be removably attached to the patient's skin.

5. The surgical incision guide means as set forth in claim 1 in which said patch-like means is formed from a flexible material which may readily be applied to various different contoured areas of the body of the patient.

6. The surgical incision guide means as set forth in claim 2 in which said patch-like means is formed from a transparent film-like substance, and in which said patch-like means includes second indicia means in the form of a narrow conspicuous annular band affixed thereto and disposed circumjacent to the central opening.

7. The surgical incision guide means as set forth in claims 1, 2, 3, 4, 5 or 6 in which said centrally disposed opening has a diameter D and said delineation means is oblong in shape having a major axis L and a minor axis W, and in which the magnitude of said minor axis W is a nominal one and one-half times greater than that of said diameter D.

8. The surgical incision guide means as set forth in claim 7 in which the magnitude of said major axis L is a nominal six times greater than that of said diameter D.

9. The surgical incision guide means as set forth in claim 8 in which said oblong shaped delineation means is established by constructing two arcuate line segments of substantially equal length and converging at either of the respective ends thereof at acute angles.

10. The surgical incision guide means as set forth in claim 8 in which said oblong shaped delineation means terminates abruptly at either end of said major axis L so as to establish a pair of remotely disposed corners.

11. The surgical incision guide means as set forth in claims 1, 2, 3, 4, 5 or 6 in which said delineation means is oblong in shape having a major L and a minor axis W, and in which the magnitude of said major axis L is a nominal four times greater than that of said minor axis W.

12. Surgical incision guide means for placement over a patient's skin tumor to define an area of skin to be removed in excising the skin tumor, said guide means comprising: a flat patch means having an opening therethrough for being centered about the skin tumor; and an adhesive means for attaching said patch means to the patient's skin about the skin tumor, said patch means having a substantially elliptically shaped periphery, said periphery prescribing the outer boundary of an area to be excised with the skin tumor.

* * * * *